United States Patent
Donoghue et al.

(10) Patent No.: US 11,857,334 B2
(45) Date of Patent: Jan. 2, 2024

(54) SYSTEMS AND METHODS FOR MONITORING A SUBJECT UNDER THE INFLUENCE OF DRUGS

(71) Applicant: The General Hospital Corporation, Boston, MA (US)

(72) Inventors: Jacob A Donoghue, Boston, MA (US); Kathleen J. Koenigs, Boston, MA (US); Patrick L Purdon, Boston, MA (US); Emery N. Brown, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 612 days.

(21) Appl. No.: 16/753,628

(22) PCT Filed: Oct. 4, 2018

(86) PCT No.: PCT/US2018/054286
§ 371 (c)(1),
(2) Date: Apr. 3, 2020

(87) PCT Pub. No.: WO2019/070929
PCT Pub. Date: Apr. 22, 2019

(65) Prior Publication Data
US 2020/0237300 A1 Jul. 30, 2020

Related U.S. Application Data

(60) Provisional application No. 62/581,856, filed on Nov. 6, 2017, provisional application No. 62/567,851, filed on Oct. 4, 2017.

(51) Int. Cl.
*A61B 5/00* (2006.01)
*G16H 15/00* (2018.01)
(Continued)

(52) U.S. Cl.
CPC .......... *A61B 5/4845* (2013.01); *A61B 5/0006* (2013.01); *A61B 5/14551* (2013.01);
(Continued)

(58) Field of Classification Search
CPC . A61B 5/4845; A61B 5/0006; A61B 5/14551; A61B 5/165; A61B 5/374;
(Continued)

(56) References Cited

U.S. PATENT DOCUMENTS

2002/0059159 A1   5/2002  Cook
2008/0234598 A1   9/2008  Snyder et al.
(Continued)

FOREIGN PATENT DOCUMENTS

WO   2015069778 A1   5/2015
WO   2016022414 A1   2/2016

OTHER PUBLICATIONS

"Bewernitz, Michael, et al., Electroencephalogram-based pharmacodynamic measures: a review, 2012, International Journal of Clinical Pharmacology and Therapeutics, vol. 50, pp. 162-184" (Year: 2012).*
(Continued)

*Primary Examiner* — Joseph M Dietrich
*Assistant Examiner* — Michael T. Holtzclaw
(74) *Attorney, Agent, or Firm* — Quarles & Brady LLP

(57) ABSTRACT

Systems and methods for monitoring a subject under, or suspected to be under, the influence of one or more drugs are provided. In one aspect, a method comprises controlling one or more sensors of a monitoring device to acquire physiological signals from a subject suspected to be under the influence of one or more drugs, and assembling a set of physiological data using the acquired physiological signals. The method also includes generating, using a processor of the monitoring device, physiological markers characteristic
(Continued)

of the influence of the one or more drugs by analyzing the set of physiological data, and correlating the physiological markers with a drug profile characterizing the one or more drugs affecting the subject. The method further includes proving to a user a report indicating the drug profile characterizing the one or more drugs affecting the subject.

20 Claims, 10 Drawing Sheets

(51) Int. Cl.
    *A61B 5/16* (2006.01)
    *A61B 5/374* (2021.01)
    *A61B 5/024* (2006.01)
    *G16H 50/20* (2018.01)
    *G16H 20/10* (2018.01)
    *A61B 5/1455* (2006.01)

(52) U.S. Cl.
    CPC .............. *A61B 5/165* (2013.01); *A61B 5/374* (2021.01); *A61B 5/6803* (2013.01); *A61B 5/7246* (2013.01); *A61B 5/7435* (2013.01); *A61B 5/7475* (2013.01); *G16H 15/00* (2018.01); *G16H 20/10* (2018.01); *G16H 50/20* (2018.01); *A61B 5/02438* (2013.01); *A61B 2562/02* (2013.01)

(58) Field of Classification Search
    CPC ..... A61B 5/389; A61B 5/6803; A61B 5/7246; A61B 5/7435; A61B 5/7475; A61B 5/02438; A61B 2562/02; A61B 5/0002; A61B 5/6898; G16H 15/00; G16H 20/10; G16H 50/20; G16H 40/63; G16H 50/70
    See application file for complete search history.

(56) References Cited

U.S. PATENT DOCUMENTS

2014/0323897 A1    10/2014   Brown et al.
2017/0049362 A1*    2/2017   Macknik ................ A61B 5/163

OTHER PUBLICATIONS

PCT International Search Report and Written Opinion, PCT/US2018/054286, dated Dec. 20, 2018, 20 pages.

* cited by examiner

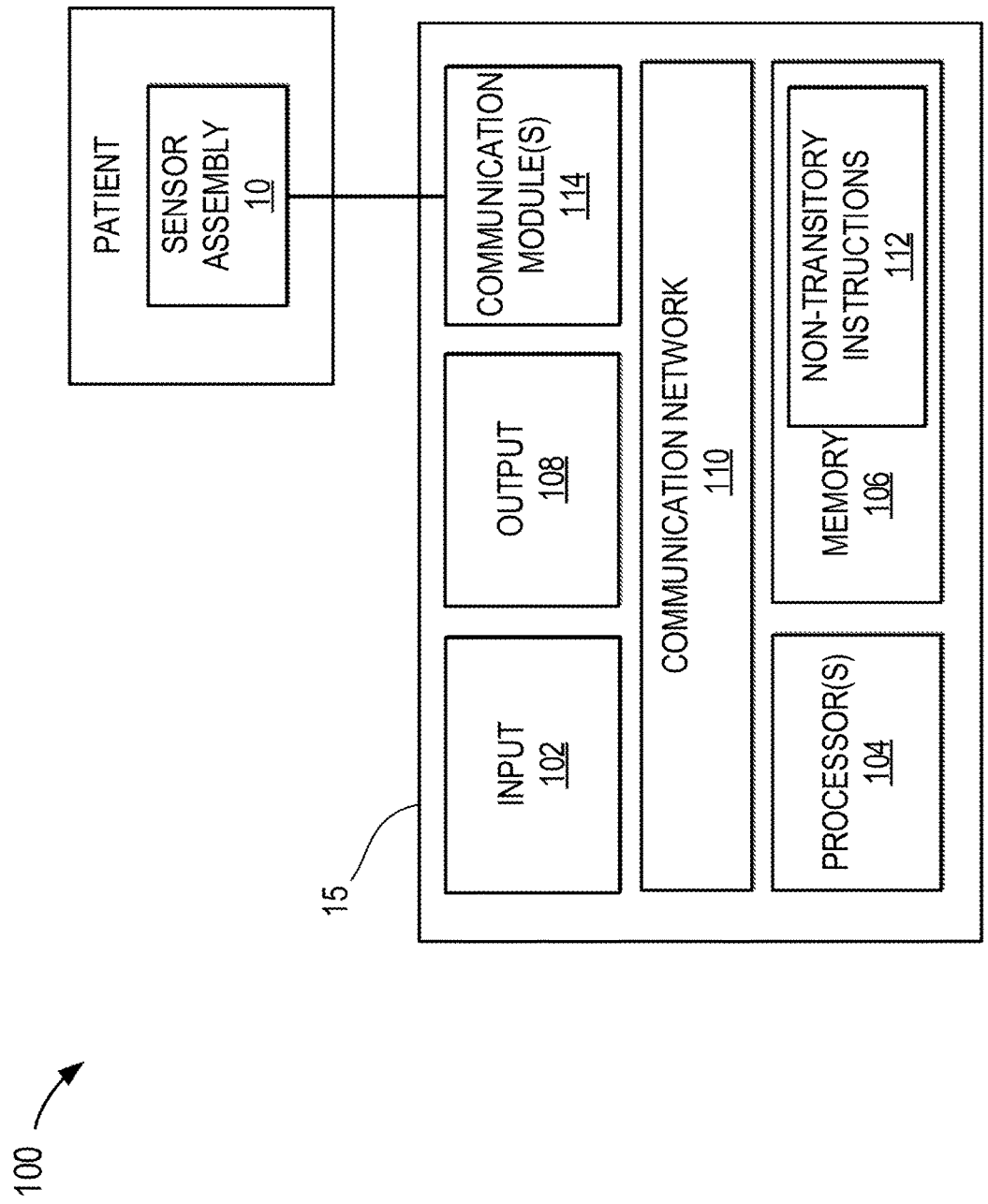

SYSTEMS AND METHODS FOR MONITORING A SUBJECT UNDER THE INFLUENCE OF DRUGS

CROSS-REFERENCE TO RELATED APPLICATIONS

The present application is a U.S. National Stage of PCT Application No. PCT/US2018/054286 filed on Oct. 4, 2018 which is based on, claims priority to, and incorporates herein in its entirety U.S. Application No. 62/567,851 filed on Oct. 4, 2017 and entitled "Materials and Methods for Point-of-Care Brain Monitoring to Aid Treatment of Overdose Symptoms," and U.S. Application No. 62/581,856 filed on Nov. 6, 2017, and entitled "System and Method for Determining a Drug Profile Using Electroencephalogram Measurements."

BACKGROUND

The present disclosure relates generally to systems and methods for brain monitoring and, in particular, to systems and methods for monitoring a subject under the influence of drugs using electroencephalogram ("EEG") and other measurements.

Last year, over 64,000 people in the United States died in opioid-related overdoses, a 22% increase from the previous year. Frequently, patients arrive under the influence of a "cocktail" of drugs, which can produce drastically different effects, and require different medical management approaches. For example, a typical cocktail might include opioids (e.g. heroin or fentanyl), benzodiazepines (e.g. "valium" or diazepam), clonidine (anti-hypertensive medication), or gabapentin (anti-convulsant medication). As appreciated, rapid and appropriate intervention are crucial, not only for saving the patient's life, but also to avoid ICU admission, which costs an average of $92,408 per substance overdose patient.

Currently, the type and amount of drugs a patient has received is only known through self-reporting. Of course, this assumes that the patient knows or is alert enough to do so. In addition, gauging the time course of drug effects and the appropriateness and efficacy of reversal medications can be difficult, if not impossible, due to the variety of possible cocktails and the different potency of the specific drugs administered (e.g. heroin versus fentanyl). In some cases, chemical point of care testing can be performed to determine potential drugs affecting a patient. However, such tests are not quantitative, can be time consuming, and often provide information for only a few classes of drugs. Most importantly, even formal toxicology tests cannot indicate the patient's state or response to the drug because these can vary significantly from person to person.

Therefore, given the above, there is a need for systems and methods for monitoring and characterizing drugs affecting a patient.

SUMMARY

The present disclosure overcomes the aforementioned drawbacks by providing systems and methods for monitoring a subject under the influence of drugs. As will become apparent from description herein, the provided systems and methods may find use in a wide range of fields, including various applications associated with clinical settings, law-enforcement, as well as commercial and industrial applications.

In accordance with one aspect of the disclosure, a method for monitoring a subject suspected to be under the influence of one or more drugs is provided. The method includes controlling one or more sensors of a monitoring device to acquire physiological signals from a subject suspected to be under the influence of one or more drugs, and assembling a set of physiological data using the acquired physiological signals. The method also includes generating, using a processor of the monitoring device, physiological markers characteristic of the influence of the one or more drugs by analyzing the set of physiological data, and correlating the physiological markers with a drug profile characterizing the one or more drugs affecting the subject. The method further includes proving to a user a report indicating the drug profile characterizing the one or more drugs affecting the subject.

In accordance with another aspect of the disclosure, a device for monitoring a subject under the influence of one or more drugs is provided. The device includes a sensor assembly comprising one or more sensors configured to acquire physiological signals from a subject, and a monitoring unit including a communication module configured to receive data from the sensor assembly and transmit data thereto. The monitoring unit also includes at least one processor configured to execute instructions stored in a memory to control the one or more sensors, using the communication module, to assemble a set of physiological data using acquired physiological signals, and generate physiological markers characteristic of the influence of the one or more drugs by analyzing the set of physiological data. The at least one processor is also configured to correlate the physiological markers with a drug profile characterizing the one or more drugs affecting the subject, and generate a report indicating the drug profile characterizing the one or more drugs affecting the subject. The device also includes a display for providing the report to a user.

In accordance with yet another aspect of the disclosure, a method for determining a mental state of a subject is provided. The method includes controlling one or more sensors of a monitoring device to acquire physiological signals from a subject, and analyzing, using a processor of the monitoring device, physiological data associated with physiological signals to identify one or more mental state indicators. The method also includes, determining, using the processor, a physiological stability of the subject based on the mental state indicators, and generating a report indicating the physiological stability of the subject.

The foregoing and other advantages of the invention will appear from the following description.

BRIEF DESCRIPTION OF THE DRAWINGS

The present invention will hereafter be described with reference to the accompanying drawings, wherein like reference numerals denote like elements.

FIG. 1A is a schematic diagram of an example system, in accordance with aspects of the present disclosure.

DETAILED DESCRIPTION

Figure 1B:
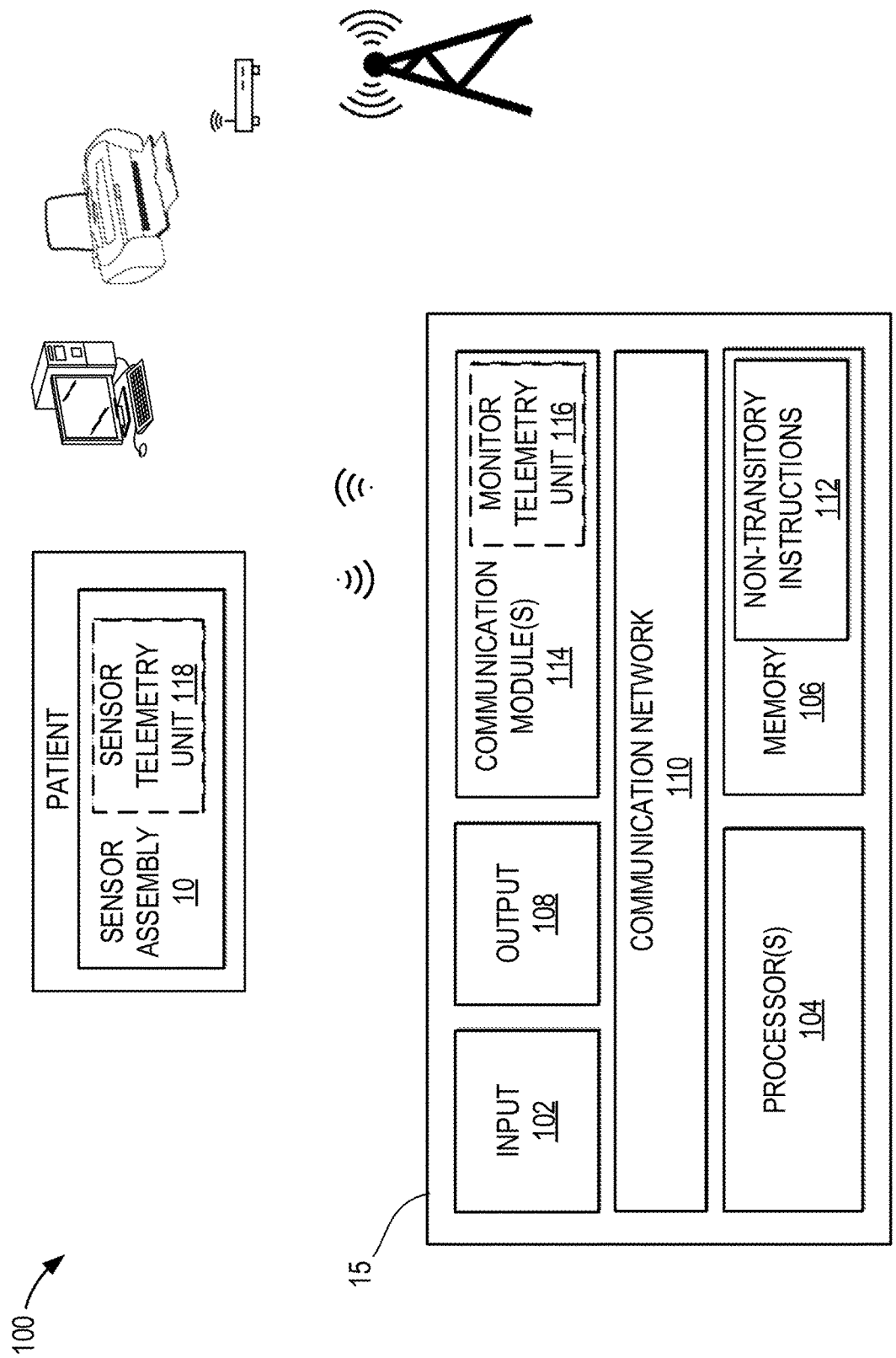
FIG. 1B is a schematic diagram of another example system, in accordance with aspects of the present disclosure.

Almost 80 years ago, Gibbs, Gibbs and Lenox demonstrated that systematic changes can occur in electroencephalogram ("EEG") and patient arousal measurements with increasing doses of administered ether or pentobarbital. They recognized the practical application of these observations to be used as measures of depth-of-anesthesia. Several subsequent studies reported on the relationship between electroencephalogram activity and the behavioral states of general anesthesia. Faulconer showed in 1949 that a regular progression of the electroencephalogram patterns correlated with the concentration of ether in arterial blood. Linde and colleagues used the spectrum—the decomposition of the electroencephalogram signal into the power in its frequency components—to show that under general anesthesia the electroencephalogram was organized into distinct oscillations at particular frequencies. Bickford and colleagues introduced the compressed spectral array or spectrogram to display the electroencephalogram activity of anesthetized patients over time as a three-dimensional plot (power by frequency versus time). Fleming and Smith devised the density-modulated or density spectral array, the two-dimensional plot of the spectrogram for this same purpose. Levy later suggested using multiple electroencephalogram features to track anesthetic effects. Since the 1990s, depth-of-anesthesia resulting from administration of anesthetic agents has been tracked using EEG recordings and behavioral responses.

Herein, the inventors recognize that narcotic or pharmaceutical drugs often responsible for overdose can be either identical to routinely-used anesthetic drugs (e.g. opioids), or in the same drug class (e.g. clonidine and dexmedetomidine as alpha-2 adrenergic agonists), or work through similar mechanisms (e.g., gamma-aminobutyric acid or GABA). Therefore, it is a discovery of the present disclosure that EEGs and other physiological measurements, may be utilized to identify or characterize drugs affecting a subject. In particular, based on pre-determined signatures, a drug profile identifying the different drugs or drug doses acting on the subject can then be determined.

It is also recognized herein that different levels and types of intoxication can affect the amplitude and duration of the evoked brain-wave response to sensory stimuli. Therefore, in some aspects, sensory stimulations can also be administered using systems and methods herein to elucidate higher or lower-order cognitive processing involvement. For instance, time-locked sensory stimuli, such as visual, auditory, tactile, olfactory, and other stimuli, may be provided. Evoked patient-specific responses, detected using measurements of EEG activity, for instance, could then be compared with pre-determined baseline responses.

In addition, the present systems and methods may also be used to assess mental status. For instance, questions from the standardized clinical tests, such as the "miniature mental status exam," reaction time or memory tests may be provided, performance to the tests may be compared to established or derived baseline ranges to indicate differences or deviations from normal. The results may then be used to determine mental status, level of intoxication, or patient response to therapy, for instance. In some aspects, a combination of physiological measurements, stimulation and performance measurements may be utilized to identify drugs affecting a patient as well as determine mental states or physiological stability of a patient. In this manner, drug levels intoxication or overdose, as well as a patient's condition or response to therapy may be identified.

As will become apparent from description below, systems and methods provided herein afford a number of advantages not previously achievable. This is because patients under the influence often do not know, or are unable to inform on the type(s) and amounts of drugs taken, thereby making treatment challenging. Also, the time course of drug effects and appropriateness and efficacy of reversal medications can be difficult to ascertain. Moreover, standard toxicology tests available in the clinic cannot indicate the patient's individual state or likely drug response due to patient variability. To solve these problems, the present disclosure provides systems and methods that can determine a subject's specific drug profile or mental state, thereby providing valuable information that allows clinicians, or other professionals, to act accordingly. Therefore, the present disclosure provides a significant technological improvement in a variety of fields, including patient monitoring for clinical applications, law-enforcement, as well as commercial and industrial applications.

Turning now to FIGS. 1A and 1B, block diagrams of an example system 100, in accordance with aspects of the present disclosure, are shown. In some embodiments, the system 100 may be any general-purpose computing system or device, such as a personal computer, workstation, cellular phone, smartphone, laptop, tablet, and the like. In this regard, the system 100 may be a system designed to integrate a variety of software, hardware, capabilities and functionalities. Alternatively, and by way of particular configurations and programming, the system 100 may be a special-purpose system or device, such as a dedicated monitoring or drug detection/overdose system or device.

In some implementations, the system 100 can be hand-held, portable or wearable. Also, the system 100 may operate autonomously or semi-autonomously based on user feedback or other input or instructions. Furthermore, the system 100 may operate as part of, or in collaboration with, various computers, systems, devices, machines, mainframes, networks, and servers.

As shown in FIGS. 1A and 1B, the system 100 may generally a sensor assembly 10 and a monitoring unit 15 including an input 102, at least one processor 104, a memory 106, an output 108, and a communication network 110. The system 100 may include one or more housing containing the various elements of the system 100.

In particular, the sensor assembly 10 may include one or more sensors for detecting physiological signals from a subject. By way of example, the sensor assembly 10 may include various EEG sensors, galvanic skin response (GSR) sensors, electrocardiographic sensors, heart rate sensors, blood pressure sensors, oxygenation sensors, oxygen saturation (SpO2) sensors, ocular microtremor sensors, and others. As such, the sensor assembly 10 may also include various elements or components, such harnesses, headbands, caps, straps, belts and the like, configured to secure the sensors to the subject. In some configurations, the sensor assembly 10 may also include various electronic and hardware components connected, or connectable, to the sensors that is configured for pre-processing the physiological signals detected by the sensors (e.g. amplifiers, filters, integrated circuits, microchips, analog-to-digital and digital-to-analog converters, and so on).

In one embodiment, the sensor assembly 10 includes a number of electrodes. The electrodes may include scalp electrodes, intracranial electrodes, cutaneous electrodes, subdural electrodes, subcutaneous electrodes, and others, configured to detect brain activity in a subject. The electrodes may be arranged in an array, and constructed using various materials including conductors, semiconductors, insulators, adhesives, plastics, and other materials. For example, the electrodes may be formed using gold, silver, copper, aluminum, stainless steel, tin, and other materials.

Movement of subject may also be helpful in identifying the specific drug(s) affecting a subject, or to determine efficacy of a treatment. Therefore, the sensor assembly 10 may also include position, orientation, and/or movement sensors (e.g. accelerometers, GPS sensors, and others) for detecting the position, orientation or movement of the subject. Furthermore, in some configurations, the sensor assembly 10 may also include various elements or devices that are configured to stimulate a subject by way of visual, auditory, tactile, olfactory, and other stimuli. In some configurations, position/orientation/movement sensors, stimulation elements/devices, and other sensors of the sensor assembly 10, may be included in the housing of the monitor unit 10, or in a separate housing or assembly, as shown in FIG. 1.

The input 102 may include various input elements configured for receiving selections and operational instructions from a user or subject. For example, the input 102 may include a mouse, keyboard, touchpad, touch screen, microphone, buttons, and the like. The input 102 may also include various drives and receptacles for receiving various data and information, such as flash-memory drives, USB drives, CD/DVD drives, and other receptacles.

Generally, the processor 104 may be configured to carry out various steps for operating the system 100. As such, the processor 104 may include one or more general-purpose processors, such as computer processing units (CPUs), graphical processing units (GPUs), and so on. In some implementations, the processor 104 may also be configured to perform methods, or steps thereof, in accordance with aspects of the present disclosure. To do so, the processor 104 may be programmed to execute instructions corresponding to the methods or steps. As shown in FIGS. 1A and 1B, such instructions may in stored in the memory 106, in the form of non-transitory computer readable-media 112, or alternatively elsewhere in a data storage location. Alternatively, or additionally, the processor 104 may also include various processing units or modules that are hard-wired or pre-programmed to execute such instructions. As such, the processor 104 may be an application-specific processor, or include one or more application-specific processing units or modules.

The memory 106 may store a variety of information and data, including instructions executable by the processor 104, as described. In some implementations, the memory 106 may have stored therein various pre-determined markers, indicators or signatures associated with different drugs, drug classes, drug combinations, and drug doses. Alternatively, or additionally, these may be stored in another accessible data storage location, such as a database or server. The markers, indicators or signatures may be stored in the form of specific numerical values, numerical patterns, or other data representations, tabulated using various categories, including drug type, drug class, drug dose, drug combination, patient characteristics (e.g. age, size, weight, medical condition), and others.

Pre-determined markers, indicators or signatures may be generated using measurements obtained from one or more individuals. Such measurements include neural or EEG measurements, GSR measurements, electrocardiographic measurements, heart rate measurements, blood pressure measurements, oxygenation measurements, SpO2 measurements, ocular microtremor measurements, and so forth. Additionally, or alternatively, the markers, indicators or signatures may be generated based on movement, position, and orientation measurements. In some aspects, pre-determined markers, indicators or signatures may be generated using various deep learning algorithms or other deep learning techniques.

In particular, EEG markers, indicators or signatures can be specific to certain drugs, drug classes, drug combinations, drug doses and patient characteristics. These may be reflected in EEG signal amplitudes, EEG spectral power or power distribution, EEG spatio-temporal correlations, EEG phase-amplitude couplings, EEG bursts (i.e. high-amplitude EEG activity) or burst suppression (i.e. isoelectric silence), EEG coherence, EEG synchrony, as well as trends or changes therein.

Figure 3A:
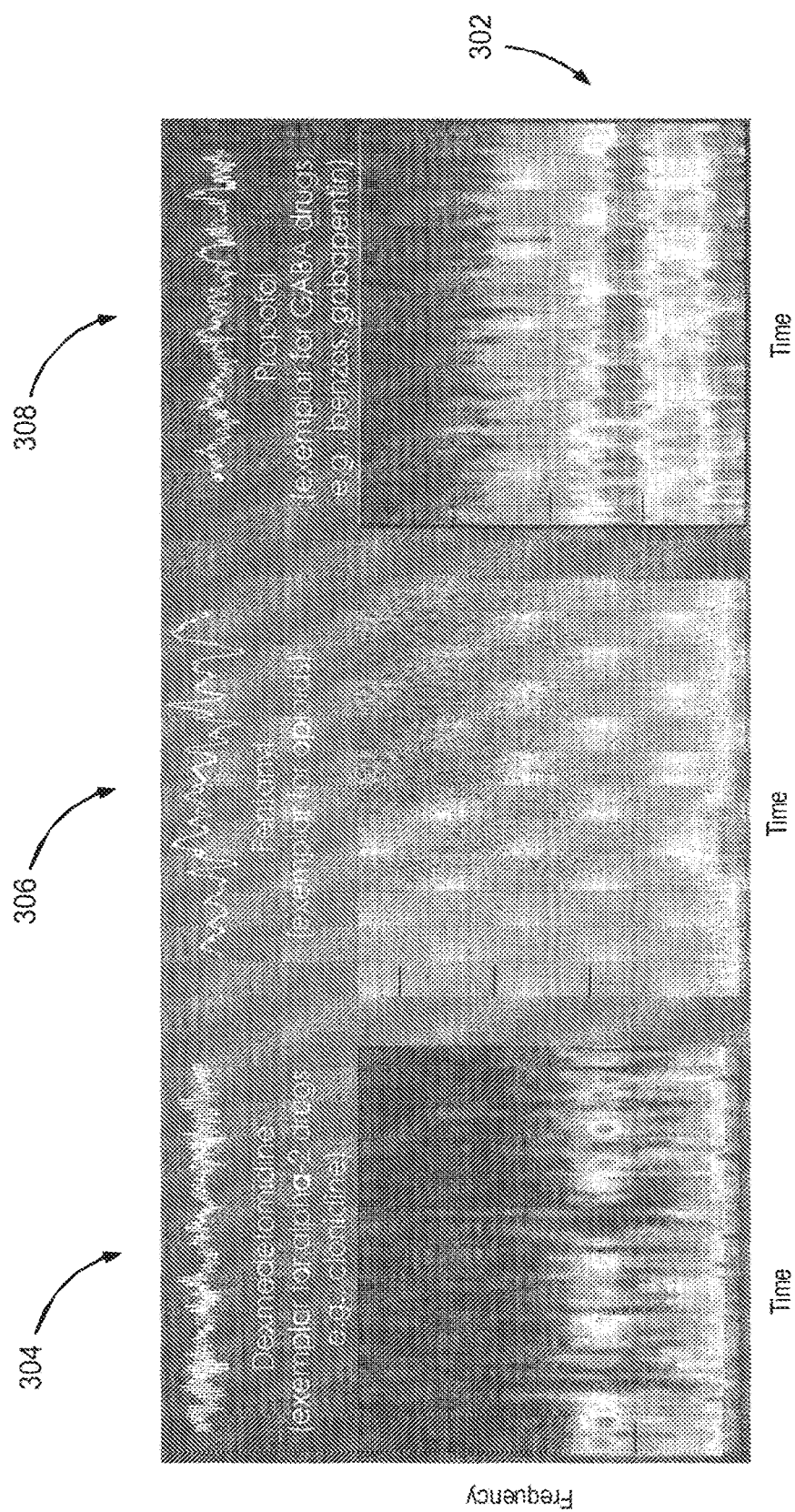
FIG. 3A is an illustration showing example signatures for different drugs, in accordance with aspects of the present disclosure.
Figure 3B:
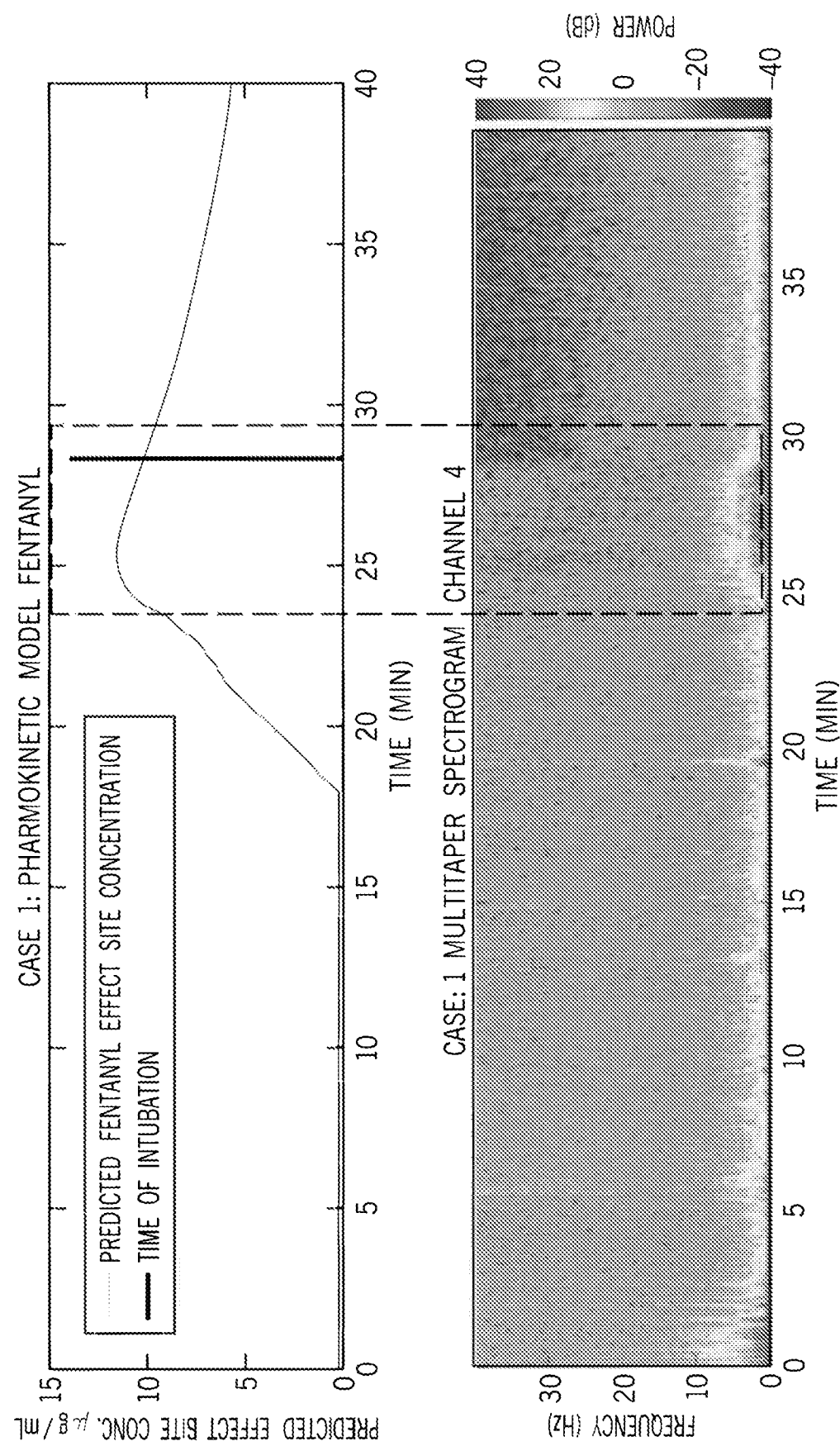
FIG. 3B is a graphical example showing a correlation between the dose of an administered drug and spectral power features, in accordance with aspects of the present disclosure.

For purposes of illustration, FIGS. 3A-B show non-limiting examples of EEG markers, indicators or signatures, in accordance with aspects of the present disclosure. Specifically, FIG. 3A shows features in spectrograms 302 that are distinct for dexmedetomidine (304), fentanyl (306) and propofol (308). As apparent from the figure, the spectrograms 302 exhibit different spectral power distributions depending on the drug being administered. Drug-specific distinctions may also be apparent in the time-series 304 data, as shown. In addition, FIG. 3B illustrates a correlation between the dose of an administered drug (e.g. fentanyl) and spectral power distribution. As shown in the spectrogram of FIG. 3B, power distribution can change based on drug dose.

Figure 8:
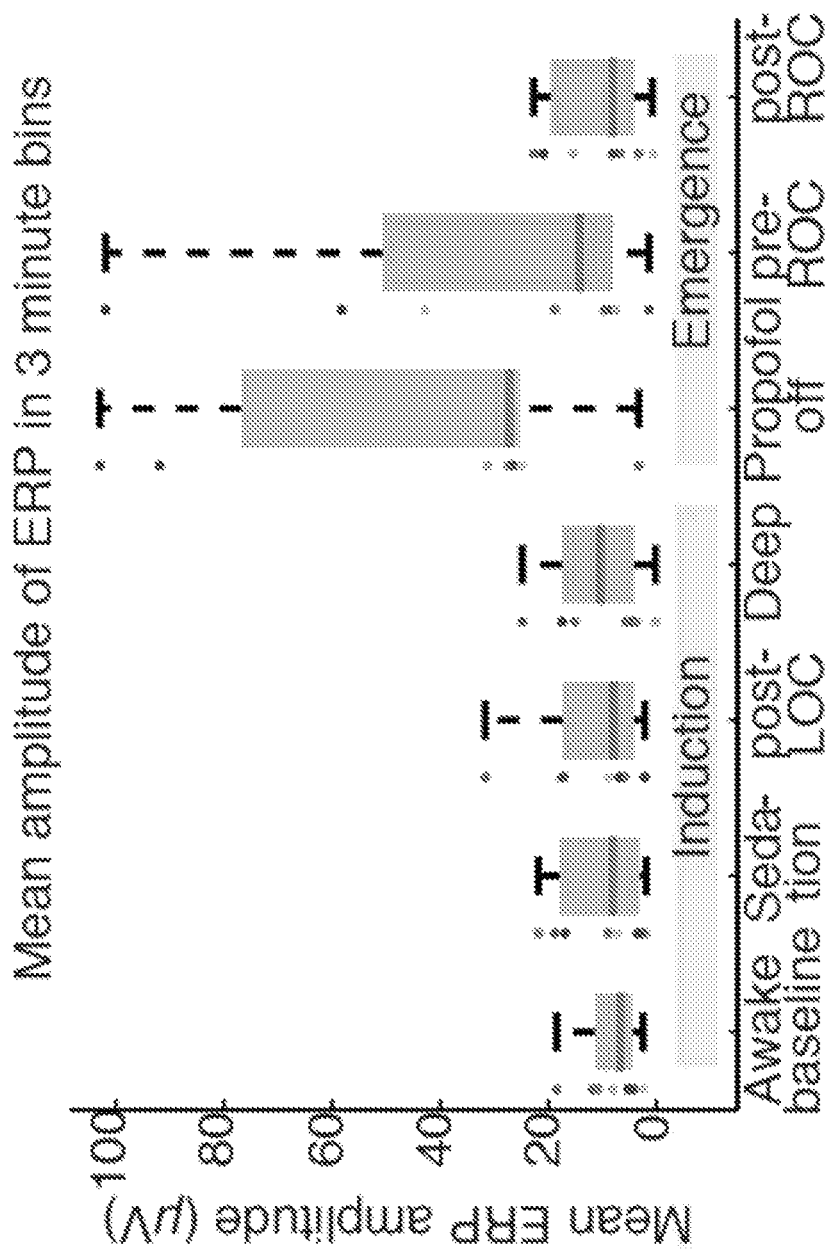
FIG. 8 is a graph showing mean evoked response potential (ERP) amplitudes obtained from eight subjects undergoing induction and emergence from anesthesia using propofol.

During anesthesia, auditory stimuli can elicit evoked potentials across various electrodes positioned about a subject. By way of example, FIG. 8 shows a graph of mean evoked response potential (ERP) amplitudes obtained from eight subjects undergoing induction and emergence from anesthesia using propofol. As shown in the figure, ERP amplitudes are generally small at baseline, sedation and post-loss-of consciousness (LOC). By contrast, ERP amplitudes are large after propofol is turned off and before return-of-consciousness (ROC). Therefore, it is envisioned that ERP signatures, as ascertained from amplitude, duration, spectral power, and other features, may be used to determine a state of a subject, in accordance with aspects of the present disclosure.

Figure 6:
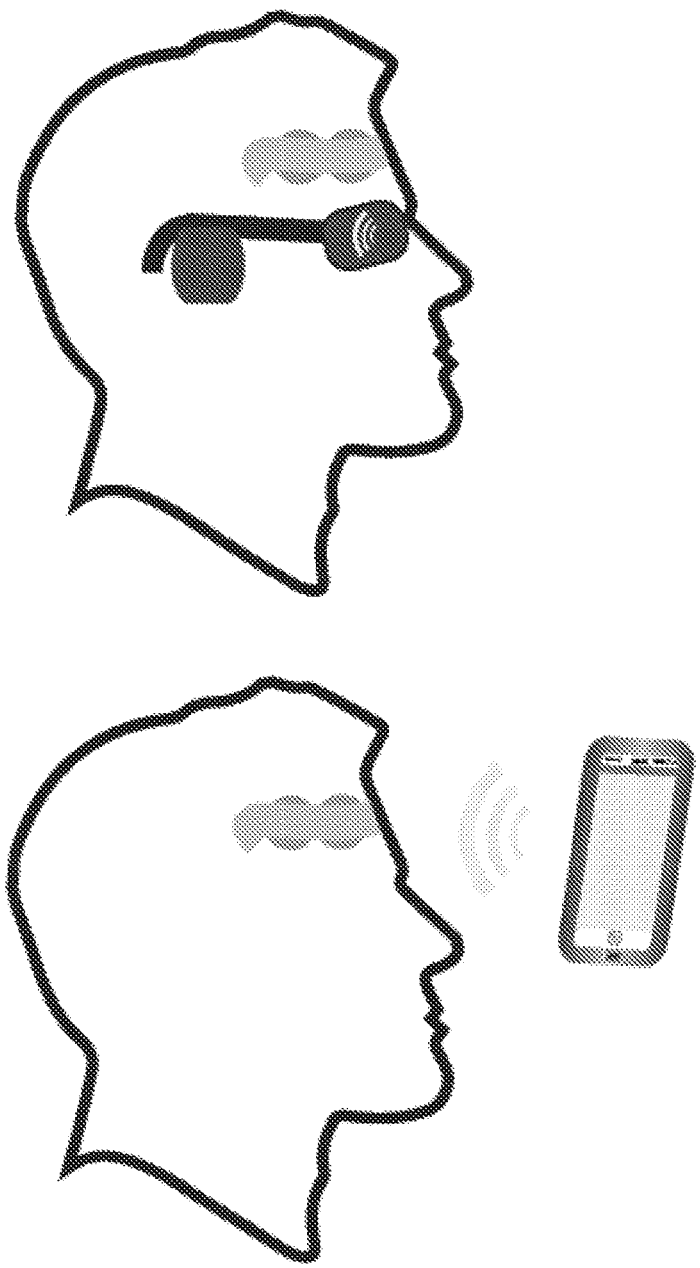
FIG. 6 is an illustration showing another embodiment of the system shown in FIG. 1.
Figure 6:
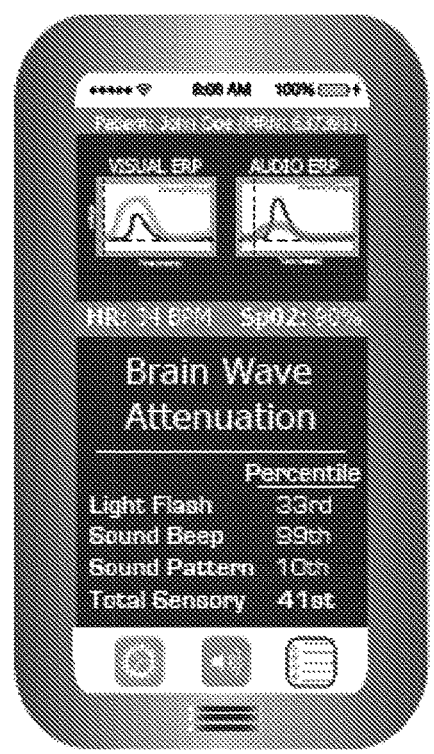

Referring again to FIGS. 1A and 1B, the output 108 may be configured to provide a report to a user. In addition, in some configurations, the output 108 may also include various elements or devices to stimulate a subject, for instance, using visual, auditory, tactile, olfactory, and other stimuli. As such, the output 108 may include various output or stimulation elements, including displays, screens, speakers, LCDs, LEDs, vibration elements, tactile or textured elements, olfactory elements, temperature elements, scent elements, and so on. Although the output 108 is shown in FIGS. 1A and 1B as a single element, as mentioned, the output 108 may include multiple output elements, not all of which need to be contained in the same housing or be part of the same device. For example, as shown in FIG. 6, a visual stimulus may be provided to a subject via a separate visual device (e.g. wearable glasses or goggles). In some configurations, output or stimulation elements may be alternatively, or additionally, included in the sensor assembly 10, as described.

The system 100 may be configured to communicate wirelessly with various external computers, systems, devices, machines, cellular towers, cellular/mobile networks mainframes, and servers, As such, the system 100 may also include a number communication modules 114 configured for transmitting and receiving signals, data and information wirelessly. In some implementations, as shown in FIG. 1B, the communication module 114 includes a monitor telemetry unit 116, configured to communicate wirelessly (e.g. using WiFi or Bluetooth) with a sensor telemetry unit 118 on the sensor assembly 10.

The communication module 114 may also be capable of wired communication, as shown in FIG. 1A. To this end, the communication module 114 may include various communication hardware, and ports to facilitate communication. Example ports include serial ports, parallel ports, Digital Visual Interfaces, Display ports, eSATA ports, SCSI ports, PS/2 ports, USB ports, Ethernet ports, and others.

In some implementations, the processor 104 may be configured to control the sensor assembly 10 via the communication module 114 to acquire physiological signals, and other information associated with a subject. Specifically, the processor 104 may control the operation sensors in the sensor assembly 10, as well as other sensors or hardware configured in the sensor assembly 10 or monitor unit 15, such as various positional/movement sensors, digitizers, samplers, filters, data acquisition cards, and so on. The processor 104 may then generate or receive data corresponding to acquired signals, and analyze the data to identify data features or signatures corresponding to one or more drugs, or drug doses. In the analysis, the processor 104 may assemble and process the data in any number of ways. In particular, the processor 104 may assemble a time-series or a time-frequency representation of the data. For example, the processor 104 may generate power and coherence spectra or spectrograms, using the EEG signals, by performing an analytic decomposition or applying a multi-taper technique. The processor 104 may carry out a number of other processing or pre-processing steps to generate markers, indicators or signatures indicating an influence of drugs on the subject. As described, the processor 104 may also take into consideration patient characteristics in the analysis.

By correlating the generated markers, indicators or signatures with pre-determined information, the processor 104 may then determine the drug profile of the subject. In doing so, the processor 104 may compare individual signal/data features or patterns to pre-determined ones stored in a memory or database, as described. For instance, the processor 104 may compare individual measurements to pre-determined thresholds, values or ranges corresponding with specific drugs, drug types or classes, drug combinations, or drug doses. In addition, the processor 104 may also compare assembled waveforms or time-series data, spectra, spectrograms, and features or patterns therein, with pre-determined ones.

The drug profile determined by the processor 104 may characterize the various drugs affecting the subject. For example, the drug profile may identify the drug (e.g. by drug type or drug class), or combinations of drugs present in a subject's body, as well as the respective drug doses (e.g. absolute or relative dose). Non-limiting examples of drugs in a drug profile may include opioids, stimulants, depressants, benzodiazepines, tetrahydrocannabinols, alpha-2 agonists, ketamines, clonidines, tetrahydrocannabinols, alcohol, and so on.

In some implementations, the processor 104 may also be configured to control the output 106, or other stimulation elements or devices in the sensor assembly 10 or monitoring unit 15, to provide various stimuli and performance tests to the subject. Based on the response to the stimulus, input by the subject to the performance test, as well as physiological measurements, the processor 104 may determine a drug profile, or mental states or mental status of the subject. To do so, the processor 104 may apply various algorithms taking into consideration markers, indicators or signatures based on physiological measurements, movement/position/orientation information, stimulus measurements, and performance measurements, as well as the strength of correlation of these measurements with specific drugs or mental status. The processor 104 may then generate a report and provide it to a user via output 108, for instance, in substantially real time.

Figure 4:
FIG. 4 is an illustration showing an embodiment of the system shown in FIG. 1.
Figure 7:
FIG. 7 is an illustration showing yet another embodiment of the system shown in FIG. 1.

The report may have any form and include a variety of information. For instance, as shown in the non-limiting example of FIG. 4, the report may provide an indication of measured brain activity and acquired physiological measurements, as well as a subject's drug profile, among other information. The report may also indicate performance or stimulus results, as shown in the non-limiting examples of FIGS. 6 and 7. In addition, the report may provide additional information to a user, for instance, in the form of instructions for a performance test, patient information/characteristics, and so forth, as shown in FIG. 7.

Figure 2:
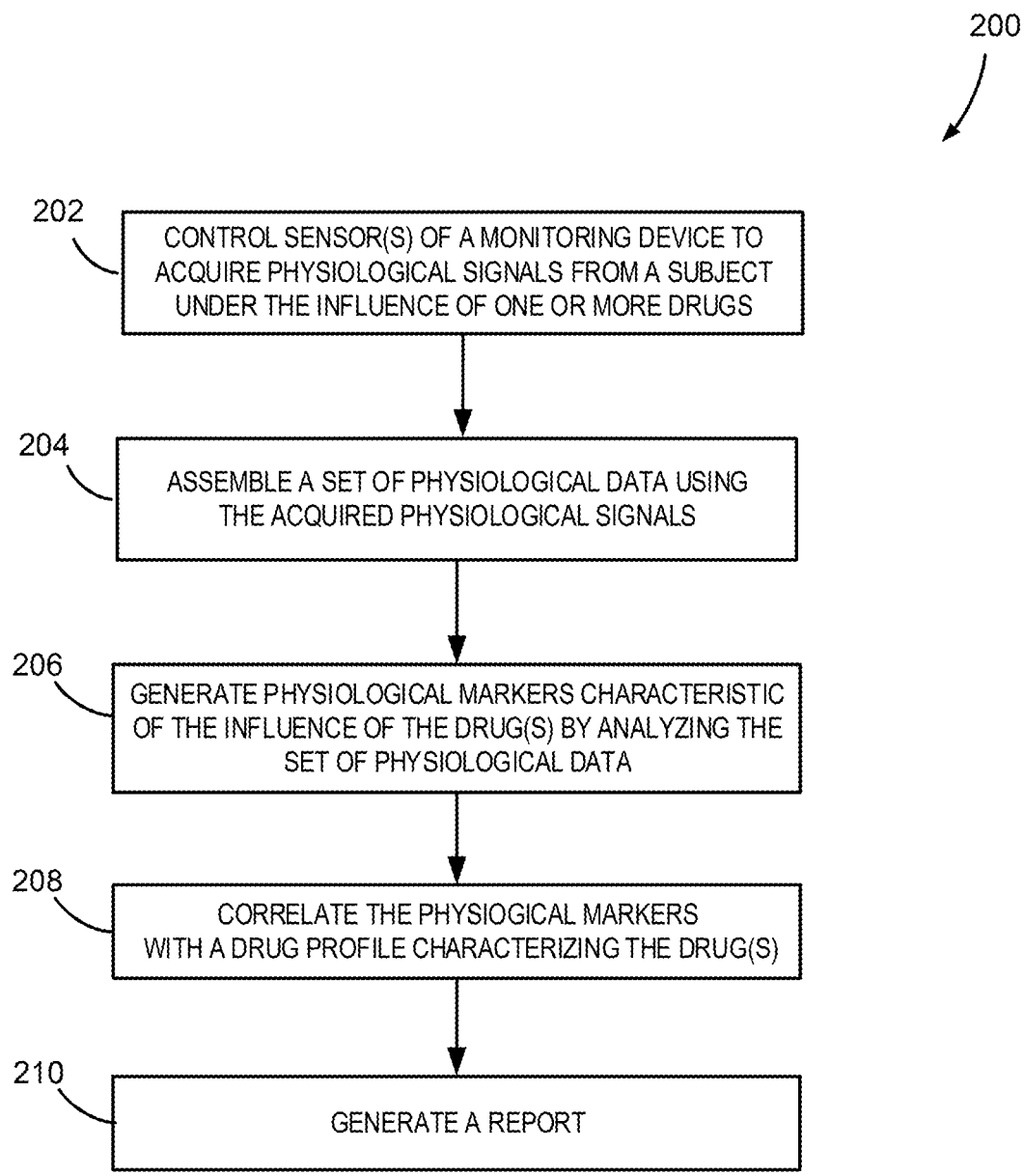
FIG. 2 is a flowchart setting forth steps of a process, in accordance with aspects of the present disclosure.

Turning now to FIG. 2, a flowchart setting forth steps of a process 200, in accordance with aspects of the present disclosure, is shown. The process 200, or various steps therein, may be carried out using any suitable device, apparatus or system, such as the system 100 described with reference to FIG. 1. Steps of the process 200 may be implemented as a program, firmware, software, or instructions that may be stored in non-transitory computer readable media and executed by a general-purpose, programmable computer, processor or other suitable computing device. In some implementations, steps of the process 200 may also be hardwired in an application-specific computer, processor or dedicated module.

The process 200 may begin at process block 202 with controlling one or more sensors of a monitoring device to acquire physiological signals from a subject that is under, or suspected to be under, the influence of one or more drugs. As described, this may include acquiring EEG signals, EMG signals, heart rate signals, and others. In some aspects, the physiological signals may be acquired before, during or after a stimulus or performance test is provided to the subject. Alternatively, data corresponding to the physiological signals may be retrieved from a memory or other data storage location. As described, in additional to physiological signals, other measurements may be acquired at process block 202, including position, orientation, or movement measurements.

Then, a processing of acquired physiological signals, and other measurements, may be carried out. For example, the physiological signals and other measurements may be pre-processed (e.g. sampled, filtered, scaled, digitized, integrated, and so forth). In some aspects, as indicated by process block 204, the physiological signals may be assembled into a set of physiological data that reflects a specific form or data representation, such as waveform or time-series, spectral or time-frequency representations, and others. To this end, various data processing or transformation techniques may be applied at process block 204. For example, an analytic decomposition of the EEG signals (e.g. multitaper) may be used to generate a time-frequency representation of the EEG signals.

The set of physiological data, and other acquired measurement data, may then be analyzed at process block 206 to generate various markers, indicators or signatures characteristic of the influence of the drug(s) on the subject. As described, this may include identifying specific features or patterns in the data. This analysis may be carried using various algorithms configured to identify such features or patterns. For example, one algorithm might identify whether measurements, or quantities derived therefrom, exceed one or more pre-determined thresholds or ranges. Another algorithm might identify a trend or change from a baseline or reference. Yet another algorithm might identify a spatio-temporal pattern, or change thereof.

Then, at process block 208, a drug profile of the subject may be determined by correlating the physiological markers, and other indicators or signatures, with a drug profile characterizing the drug(s) affecting the subject. As described, the drug profile may indicate various drugs, drug classes, doses and combinations of drugs, such as opioids, benzodiazepines, alpha-2 agonists, ketamine, alcohol and others, affecting a subject As described, responses of the subject to a stimulus, queries or a performance test may be used to aid in determining the drugs affecting the subject. In addition, such response may be indicative of underlying mental states. Such mental states can reflect various cognition or brain conditions, mental status, mental capacity, memory, likelihood of response to therapy, stability of the subject's physiological status, and so on. Therefore, in conjunction with, or separate from the analysis at process blocks 206 and 208, an analysis may also be performed to identify a mental state of the subject. To this end, the analysis may be performed using various physiological markers, indicators or signatures, generated based on measurements corresponding to an administered stimulus or performance test.

A report may then be generated and provided, as indicated by process block 210. The report may include a variety of information associated with the determined drug profile. For example, the report may indicate drugs and drug doses affecting a subject, an intoxication level or overdose, and so on. In addition, the report may indicate past, current and/or future mental states or stability of the subject. The report may also include other information about the subject, as well as indications related to other physiological measurements. For example, the report may indicate heart rate, blood pressure, oxygenation, brain activity, and so on.

Figure 5:
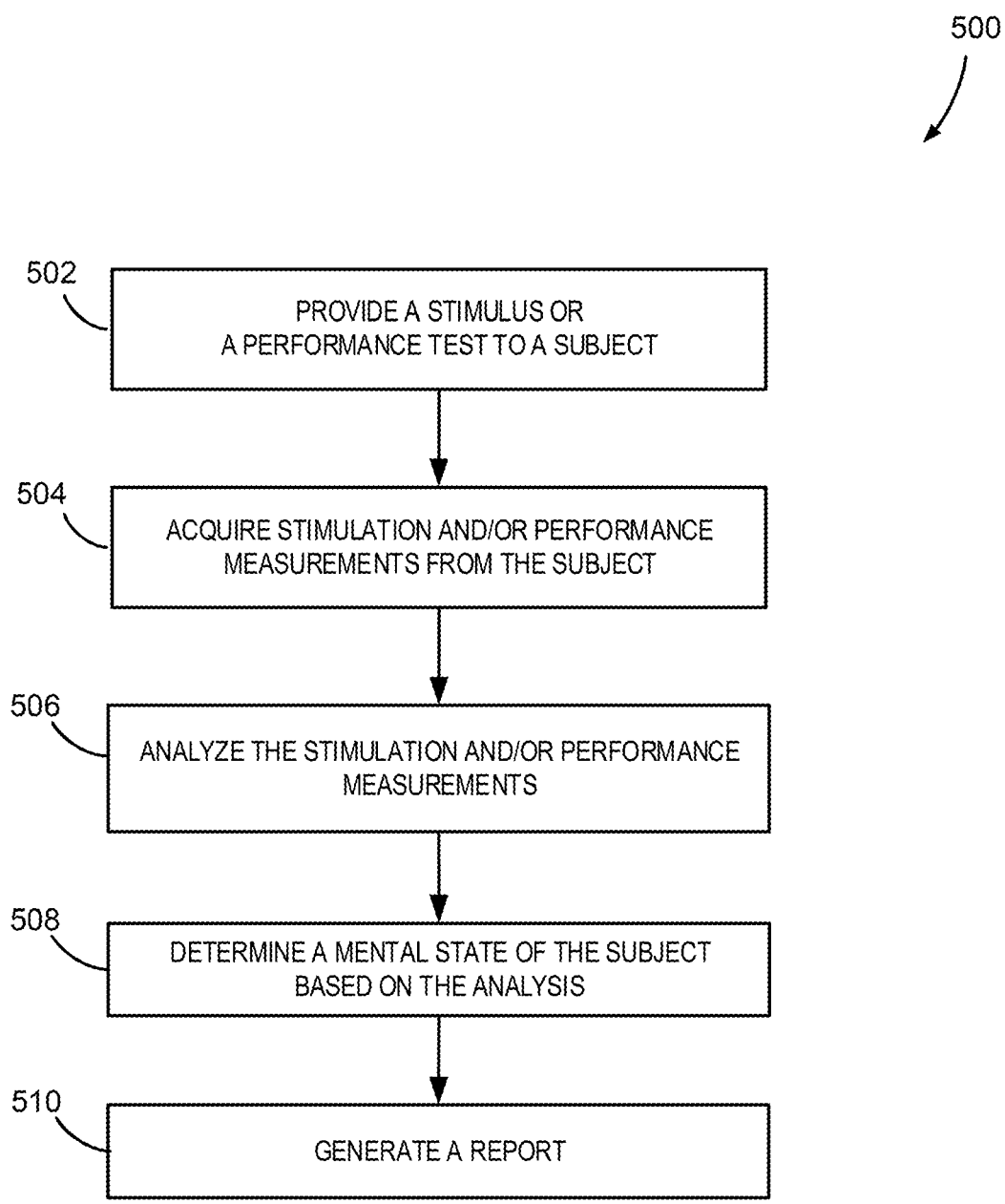
FIG. 5 is another flowchart setting forth steps of a process, in accordance with aspects of the present disclosure.

Turning now to FIG. 5, another flowchart setting forth steps of a process 500, in accordance with aspects of the present disclosure, is shown. As described, the process 500, or various steps therein, may be carried out using any suitable device, apparatus or system, such as the system 100 described with reference to FIG. 1. As above, steps of the process 500 may be implemented as a program, firmware, software, or instructions that may be stored in non-transitory computer readable media and executed by a general-purpose, programmable computer, processor or other suitable computing device. In some implementations, steps of the process 500 may also be hardwired in an application-specific computer, processor or dedicated module.

The process 500 may begin with process block 502, where a stimulus or performance test is provided to a subject. The stimulus may include a visual stimulus, an auditory stimulus, a tactile stimulus, or an olfactory stimulus, or a combination thereof. The performance test may include one or more standardized clinical tests used to determine mental status, such as the "miniature mental status exam," reaction time or memory tests, for example.

Stimulation and/or performance measurements, corresponding to evoked subject-specific physiological reactions, input or responses, may then be acquired from the subject at process block 504. An analysis of these measurements may then be performed, as indicated by process block 506. The analysis may include processing the measurements and generating various markers, indicators or signatures associated with the acquired measurements, as described. For example, various time-series, waveforms, power spectra or spectrograms, may be assembled using a number of techniques, including analytic decomposition and multi-taper techniques, and analyzed to identify specific markers, indicators or signatures indicative of the subject's state.

The identified markers, indicators or signatures may then be compared with pre-determined information to determine the subject's mental state, as indicated by process block 508. For example, features or patterns in EEG activity (e.g. amplitudes, power, spectral power distribution, and so forth) may be compared to a baseline (e.g. historical, subject-specific activity) or reference (e.g. population activity) to determine levels, changes or trends indicative of the subject's mental state, or declines thereof. Similarly, performance to the tests may be compared to established or derived baseline ranges to indicate differences or deviations from normal. The results may then be used to determine the mental state of the subject. In some aspects, the mental state of the subject may also be determined at process block 508 using a combination of physiological measurements, stimulation and performance measurements, as well as movement information, position information, and orientation information. As described, this may include applying an algorithm that takes into consideration the strength of correlation between various mental states of the subject and the various measurements and information.

A report, in any form, may then be generated and provided to a user, as indicated by process block 510. The report may include a variety of information. For instance, the report may indicate past, current and/or future mental states of the patient. Such indications may identify, for example, whether a subject's physiological status was, is, or will likely be, "stable" or "unstable." Other designations may also be used. In some implementations, as illustrated in the examples of FIGS. 6 and 7, the report may indicate current brain activity, or changes thereof due to the applied stimuli, stability. The report may further indicate scoring related to mental status, reaction time, memory, and other indicators.

Features suitable for such combinations and sub-combinations would be readily apparent to persons skilled in the art upon review of the present application as a whole. The subject matter described herein and in the recited claims intends to cover and embrace all suitable changes in technology.

The invention claimed is:
1. A method for monitoring a subject suspected to be under the influence of one or more drugs, the method comprising:
controlling one or more sensors of a monitoring device to acquire physiological signals from a subject suspected to be under the influence of one or more drugs;
assembling a set of physiological data using the acquired physiological signals;

generating, using a processor of the monitoring device, physiological markers characteristic of the influence of the one or more drugs by analyzing the set of physiological data;

decomposing the physiological data to generate a time-frequency representation of the physiological data in the form of a spectrogram;

correlating the physiological markers with a drug profile characterizing the one or more drugs affecting the subject;

providing to a user a report indicating the drug profile characterizing the one or more drugs affecting the subject.

2. The method of claim 1, wherein the method further comprises controlling a combination of electroencephalogram (EEG) sensors, electromyography (EMG) sensors, oxygenation sensors, and heart rate sensors to acquire the physiological signals.

3. The method of claim 1, wherein the method further comprises comparing the physiological markers to pre-determined signatures to determine the drug profile.

4. The method of claim 1, wherein the drug profile comprises at least one of a dose and a drug type for the one or more drugs affecting the subject.

5. The method of claim 1, wherein the one or more drugs comprises a combination of opioids, benzodiazepines, alpha-2 agonists, ketamine, tetrahydrocannabinols, and alcohol.

6. The method of claim 1, wherein the method further comprises:
providing a stimulus to the subject using a stimulation element of the monitoring device;
detecting a response evoked by the stimulus using corresponding physiological signals acquired from the subject; and
determining the drug profile of the subject based on the response.

7. The method of claim 6, wherein the stimulus is a visual stimulus, an auditory stimulus, a tactile stimulus, an olfactory stimulus, or a combination thereof.

8. The method of claim 1, wherein the method further comprises:
providing a performance test to the subject using the monitoring device;
acquiring input from the subject in response to the performance test;
determining the drug profile of the subject based on the input.

9. The method of claim 1, wherein the method further comprises:
acquiring, using position sensors, orientation sensors and movement sensors of the monitoring device, movement information, position information, orientation information, or a combination thereof, and analyzing the information to identify indicators corresponding to one or more drugs affecting the subject.

10. A device for monitoring a subject under the influence of one or more drugs, the system comprising:
a sensor assembly comprising one or more sensors configured to acquire physiological signals from a subject;
a monitoring unit comprising a communication module configured to receive data from the sensor assembly and transmit data thereto, and at least one processor configured to execute instructions stored in a memory to:
control the one or more sensors, using the communication module, to assemble a set of physiological data using the acquired physiological signals;
generate physiological markers characteristic of the influence of the one or more drugs by analyzing the set of physiological data;
decompose the physiological data to generate a time-frequency representation of the physiological data in the form of a spectrogram;
correlate the physiological markers with a drug profile characterizing the one or more drugs affecting the subject;
generate a report indicating the drug profile characterizing the one or more drugs affecting the subject; and
a display for providing the report to a user.

11. The device of claim 10, wherein the sensor assembly comprises a combination of electroencephalogram (EEG) sensors, electromyography (EMG) sensors, oxygenation sensors, heart rate sensors, position sensors, orientation sensors, and movement sensors.

12. The device of claim 10, wherein the processor is further configured to determine a drug dose, a drug type, or both, for the one or more drugs affecting the subject based on the correlation.

13. The device of claim 10, wherein the processor is further configured to compare the physiological markers to pre-determined signatures to determine the drug profile.

14. The device of claim 10, wherein the processor is further configured to control the sensor assembly or an output to provide a stimulus or a performance test, or both, to the subject.

15. The device of claim 14, wherein the stimulus comprises a visual stimulus, an auditory stimulus, a tactile stimulus, an olfactory stimulus, or a combination thereof.

16. The device of claim 14, wherein the processor is further configured to determine the drug profile of the subject by analyzing physiological data corresponding to a response evoked by the stimulus, or by analyzing input provided by the subject in the performance test, or both.

17. The device of claim 10, wherein the device further comprises sensors for generating movement information, position information, or orientation information, or a combination thereof.

18. The device of claim 17, wherein the processor is further configured to use movement information, position information, or orientation information, or a combination thereof, to identify indicators corresponding to one or more drugs affecting the subject.

19. The device of claim 10, wherein the processor is further configured to determine a brain-state signature using the set of physiological data.

20. The device of claim 19, wherein the processor is further configured to use the brain-state signature to determine a physiological stability of the subject.

* * * * *